United States Patent [19]

White

[11] 4,360,031
[45] Nov. 23, 1982

[54] DRUG DISPENSING IRRIGATABLE ELECTRODE

[75] Inventor: David L. White, Wyoming, Minn.

[73] Assignee: Medtronic, Inc., Minneapolis, Minn.

[21] Appl. No.: 186,106

[22] Filed: Sep. 11, 1980

[51] Int. Cl.³ .............................................. A61N 1/04
[52] U.S. Cl. ................................. 128/786; 128/419 P
[58] Field of Search ................................ 128/784–786, 128/419 P, 348, 642

[56] References Cited

U.S. PATENT DOCUMENTS

| | | | |
|---|---|---|---|
| 3,533,403 | 10/1970 | Woodson | 128/786 X |
| 3,568,660 | 3/1971 | Crites et al. | 128/786 |
| 3,618,613 | 11/1971 | Schulte | 128/348 |
| 3,640,269 | 2/1972 | Delgado | 128/348 X |
| 3,680,544 | 8/1972 | Shinnick | 128/786 X |

FOREIGN PATENT DOCUMENTS 2820867 11/1979 Fed. Rep. of Germany ... 128/419 P

OTHER PUBLICATIONS

USCI Catalog, Jun., 1974, pp. 1–12.

Primary Examiner—Lee S. Cohen
Attorney, Agent, or Firm—John L. Rooney; Joseph F. Breimayer; Carl A. Forest

[57] ABSTRACT

A transvenous pacing lead suitable for chronic implantation having structure which permits dispensing of drugs or other chemical agents from the ring tip electrode upon physician discretion from implant through chronic implantation. A bipolar, tined endocardial ventricular lead has a plurality of small apertures within the ring tip electrode which are connected by a tube within the lead body to a bladder at the proximal end of the lead. The bladder is detachable to permit a stylet to be passed through the tube to guide the lead during implantation. A reed valve at the distal end of the tube prevents body fluid from entering the tube. A stylet restraint prevents the stylet from damaging the reed valve during implant.

18 Claims, 9 Drawing Figures

DRUG DISPENSING IRRIGATABLE ELECTRODE

BACKGROUND OF THE INVENTION

1. Field of the Invention

The present invention relates generally to implantable medical apparatus and more specifically relates to a cardiac pacing lead having structure for dispensing chemical agents.

2. Discussion of the Prior Art

Electrodes exist which dispense chemical agents. U.S. Pat. No. 623,022 issued to Johnson teaches an early drug dispensing electrode. More recent drug dispensing electrodes are taught by U.S. Pat. Nos. 3,533,403; 3,680,544 and 3,817,241 issued to Woodson, Shinnick and Grausz, respectively. However, all of these devices are suitable for acute use only and are not usable for chronic implantation.

What is desired is a chronically implantable transvenous cardiac pacing lead having the capability for discretionary chemical treatement to enhance pacing therapy. Tests have shown that pacing thresholds can be substantially lowered using treatment of endocardial tissue by steroids and other chemical agents. Notice that the important feature for such a technique is the dispensing of the drug to the same tissue which is receiving the electrical stimulus. It is for that reason that the chronically implantable drug dispensers taught by U.S. Pat. Nos. 3,527,220; 3,692,027 and 4,146,029 issued to Summers, Ellinwood, Jr. and Ellinwood, Jr., respectively are not acceptable for this purpose. Furthermore, these chronically implantable drug dispensers are far more complex than is required here since they automatically dispense drugs over a relatively long period of time. The present invention, though chronically implantable, provides only discretionary drug therapy by direct action of the attending physician.

SUMMARY OF THE INVENTION

The present invention is a permanent transvenous cardiac pacing lead. The ring tip electrode of the pacing lead has a number of apertures through which a chemical agent may be dispensed. The apertures are connected to a tube which runs the length of the lead. By locating the tube coaxially and internally in the conducting coils of the lead, a stylet may be inserted in the tube to assist in implantation, thereby not requiring any addition to the cross-sectional area of the lead.

At the proximal end of the lead, the tube has a connector through which the stylet may be inserted and removed. After the ring tip electrode is properly positioned, the stylet is removed and the tube is coupled to a bladder. The purpose of the bladder is to implant a device of sufficient size to enable a physician to easily infuse a chemical agent. The bladder does not store the drug for subsequent release.

After implant, the physician may percutaneously dispense chemical agents via the apertures in the tip electrode by inserting a syringe into the subcutaneously located bladder. It is anticipated that the attending physician will thereby be able to readily irrigate and dispense steroids to the endocardial tissue in contact with the ring tip electrode at any time during the pacing therapy. This technique, it is felt, will alleviate trauma and permit chronic maintenance of substantially reduced pacing thresholds.

DETAILED DESCRIPTION OF THE PREFERRED EMBODIMENT

The preferred mode of the present invention herein disclosed is embodied in a drug dispensing, permanent, bipolar, transvenous, ventricular pacing lead. Those skilled in the art will readily be able to apply this invention to other configurations.

Figure 1:
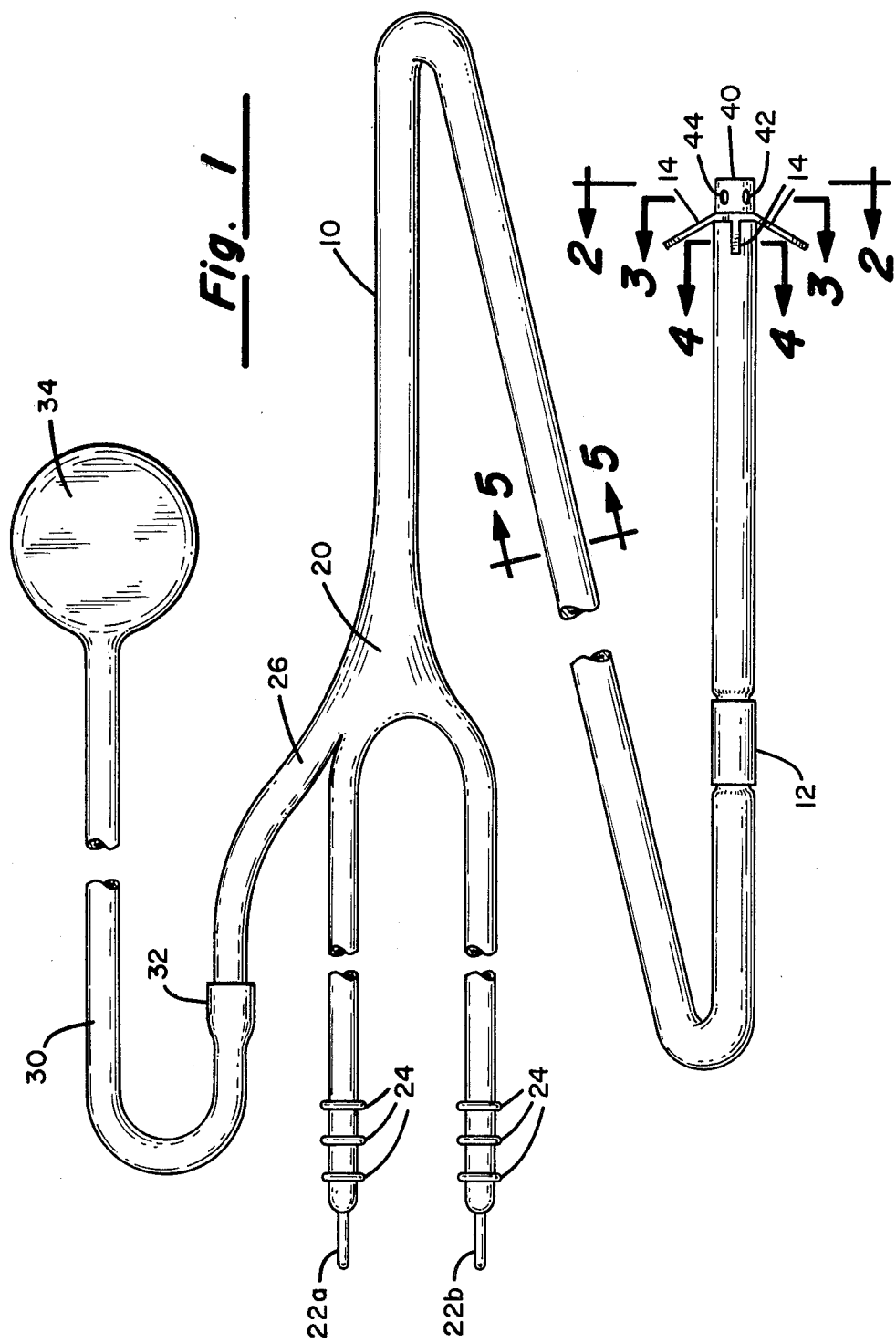
FIG. 1 is a plan view of a permanent transvenous lead incorporating the present invention.

FIG. 1 is a plan view of a pacing lead incorporating the preferred embodiment of the present invention. At the distal end of the pacing lead is ring tip electrode 40 containing side apertures 42, 44, 46 and 48 (apertures 46 and 48 are not shown). Tines 14 are used to inhibit dislodgement during chronic implantation. Ring electrode 12 serves as the indifferent electrode as with most bipolar pacing systems.

The main body of the pacing lead is covered by outer sheath 10 which is of a material substantially inert to body fluids, such as urethane or silicon rubber. Outer sheath 10 must also be an electrical insulator. Connector 20 is located at the proximal end of the pacing lead. Electrical connector pins 22a and 22b are inserted into a pulse generator to complete the electrical circuit. Electrical connector pin 22a is electrically coupled to ring tip electrode 40 via an inner conductor (not shown). Electrical connector pin 22b is electrically coupled to ring electrode 12 via an outer conductor (not shown). Sealing rings 24 are used to seal the electrical connection between electrical connector pins 22a and 22b from the ingress of body fluids.

Connector 20 also includes fluid coupling arm 26 which is shown connected to tubing 30 via fluid connector 32. Fluid coupling arm 26 is so constructed that with tubing 30 not connected at fluid connector 32, a stylet is easily inserted into fluid coupling arm 26 and thence into the tube within the main body of the pacing lead. This is accomplished by ensuring that fluid coupling arm 26 has no sharp bends and meets connector 20 and the main body of the pacing lead via smooth curves.

Bladder 34 is coupled to tubing 30 which is in turn coupled via fluid connector 32 to fluid connector arm 26. Bladder 34 is thin and quite inflexible as storage of the chemical agent is undesirable but it must be impervious to the desired chemical agents. A hypodermic syringe is percutaneously inserted into bladder 34 for dispensing drugs and irrigating the endocardial tissue. Bladder 34 must reseal itself upon removal of the hypodermic syringe. The infusate force of the hypodermic syring is sufficient to force dispensing of the drug or irrigation to the endocardial tissue via the apertures in ring tip electrode 40.

Figure 2:
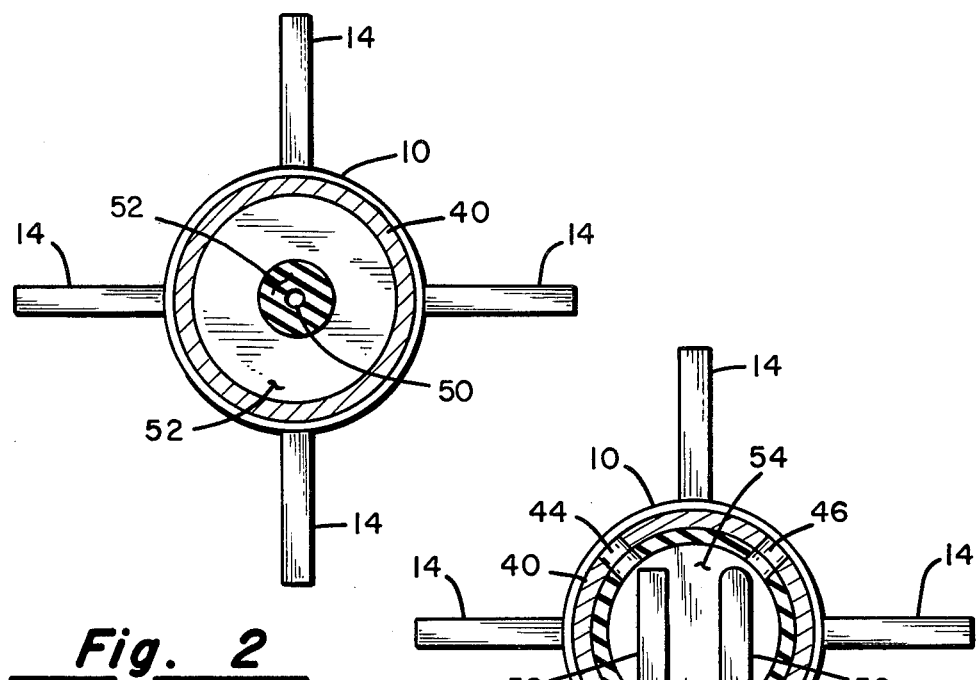
FIG. 2 is a front sectional view of the tip electrode.

FIG. 2 is a front sectional view of the distal end of the pacing lead. Ring tip electrode 40 is shown. Element 52 is a dielectric material such as silicon rubber or urethane. The cross hatched area immediately surrounding aperture 50 signifies that element 52 is cross sectioned in that area in this view. Aperture 50 is shown as in addition to apertures 42, 44, 46 and 48 (not seen in FIG. 2). These apertures are small, being of the order of 0.005 inch. Tines 14 are shown. Tines 14 are made from the same material as outer sheath 10. See U.S. Pat. No. 3,902,501 issued to Citron et al, for a further discussion of tines 14.

Figure 3:
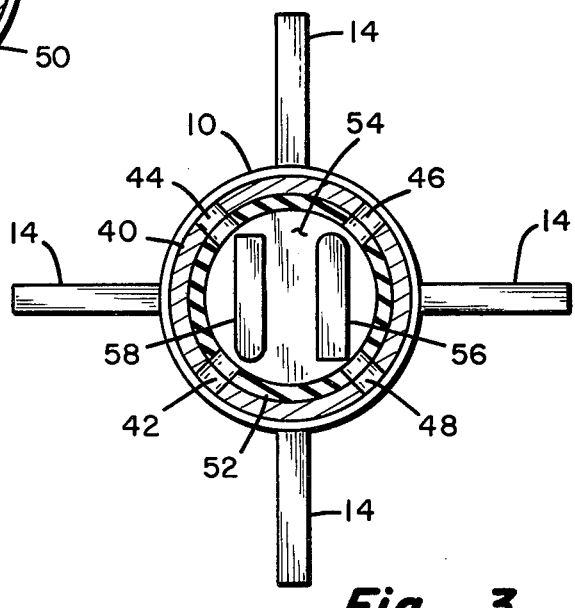
FIG. 3 is a front sectional view showing the reed valve.

FIG. 3 is a front sectional view showing reed valve assembly 54 containing individual reed valves 56 and 58. Reed valve assembly 54 permits fluid flow in a more distal direction but prevents fluid flow in a more proximal direction. This is necessary to prevent body fluids from diffusing into the tube in the main body of the pacing lead and eventually into bladder 34. Apertures 42, 44, 46 and 48 are also shown. By reference to FIG. 6, the relative position of reed valve assembly 54 may be ascertained.

Figure 4:
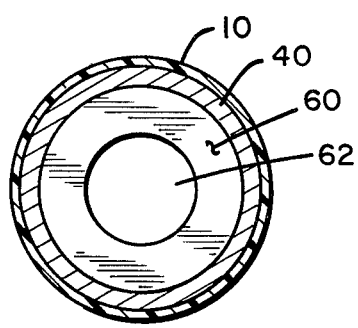
FIG. 4 is a front sectional view showing the stylet restraint.
Figure 6:
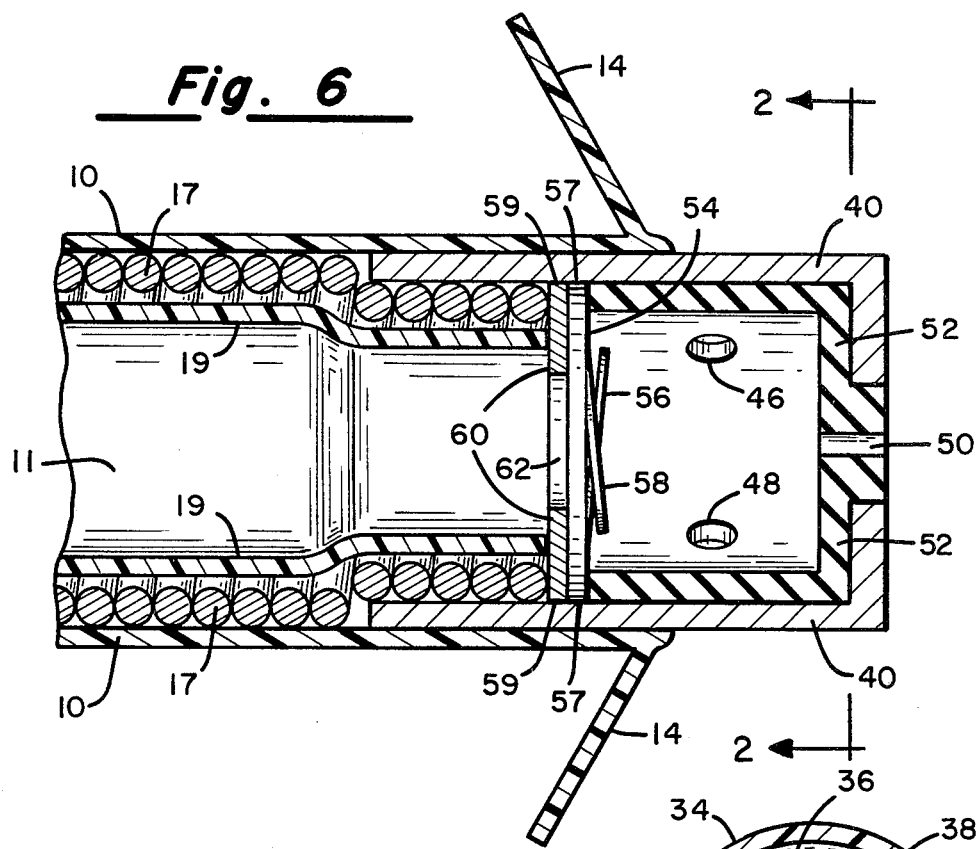
FIG. 6 is a side sectional view of the distal end of the lead.

FIG. 4 is a front sectional view showing the detail of stylet restraint 60. FIG. 6 shows the relative position of stylet restraint 60. Referring again to FIG. 4, it can be seen that stylet restraint 60 contains a relatively large aperture 62 which is on the order of 0.010-0.012 inch. This aperture provides for passage of the chemical agent to be dispensed but prohibits passage of a stylet being typically 0.014 inch or larger. Stylet restraint 60 prevents a stylet from damaging reed valve assembly 54 during implantation.

Figure 5:
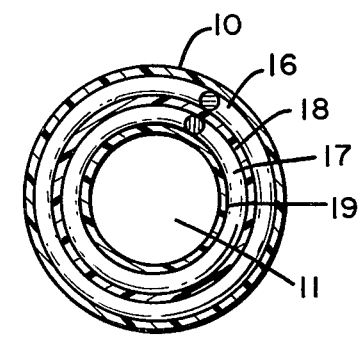
FIG. 5 is a front sectional view of the main body of the lead proximal to the indifferent electrode.

FIG. 5 is a cross-sectional view of the main body of the pacing lead as seen proximal of ring electrode 12. Outer sheath 10 insulates outer conductor 16 from exposure to body fluids and tissue. Outer conductor 16 is a helically wound coil of flexible, highly conductive wire as commonly used in cardiac pacing leads. Intermediate sheath 18 is a dielectric which insulates outer conductor 16 from inner conductor 17. Inner conductor 17 is of a construction similar to outer conductor 16. Inner sheath 19 seals and insulates inner conductor 17 from the chemical agent to be dispensed. Tube 11 is the area within inner sheath 19 through which the stylet is inserted at implantation and through which the chemical agent travels for dispensing.

FIG. 6 is a side sectional view of the distal end of the pacing lead. Outer conductor 16 and intermediate sheath 18 are terminated just distal of ring electrode 12 (not shown) using techniques known in the art. Inner conductor 17, therefore, becomes the only conductor. Inner sheath 19 defines tube 11 as explained above. Stylet restraint 60 having aperture 62 is shown in position. Reed valve assembly 54 is shown with reed valves 56 and 58. Reed valves 56 and 58 open distally as shown. Reed valve assembly 54 and stylet restraint 60 should be made of a material impervious to body fluids and the chemical agents to be dispensed. Titanium is a preferred material.

The chemical agent to be dispensed travels in a distal direction in tube 11 and passes stylet restraint 60 via aperture 62. Reed valves 56 and 58 open distally permitting the chemical agent to be forced through apertures 42, 44, 46, 48 and 50 (only 46, 48 and 50 are shown). Dielectric material 52 is silicon rubber or other suitable material which fills the void within ring tip electrode 40 thereby assuring more positive control of the dispensing process by the attending physician. The volume required to permit reed valves 56 and 58 to open and the chemical agent to flow to apertures 42, 44, 46, 48 and 50 is minimized to minimize the amount of chemical agent not immediately dispensed.

Inner conductor 17 is firmly attached to ring tip electrode 40 by welding or frictionally by swaging or crimping. Outer sheath 10 is molded or shrink fit to ring tip electrode 40 to provide a tight seal. Reed valve assembly 54 and stylet restraint 60 are attached to electrode 40 by welds 57 and 59.

Figure 7:
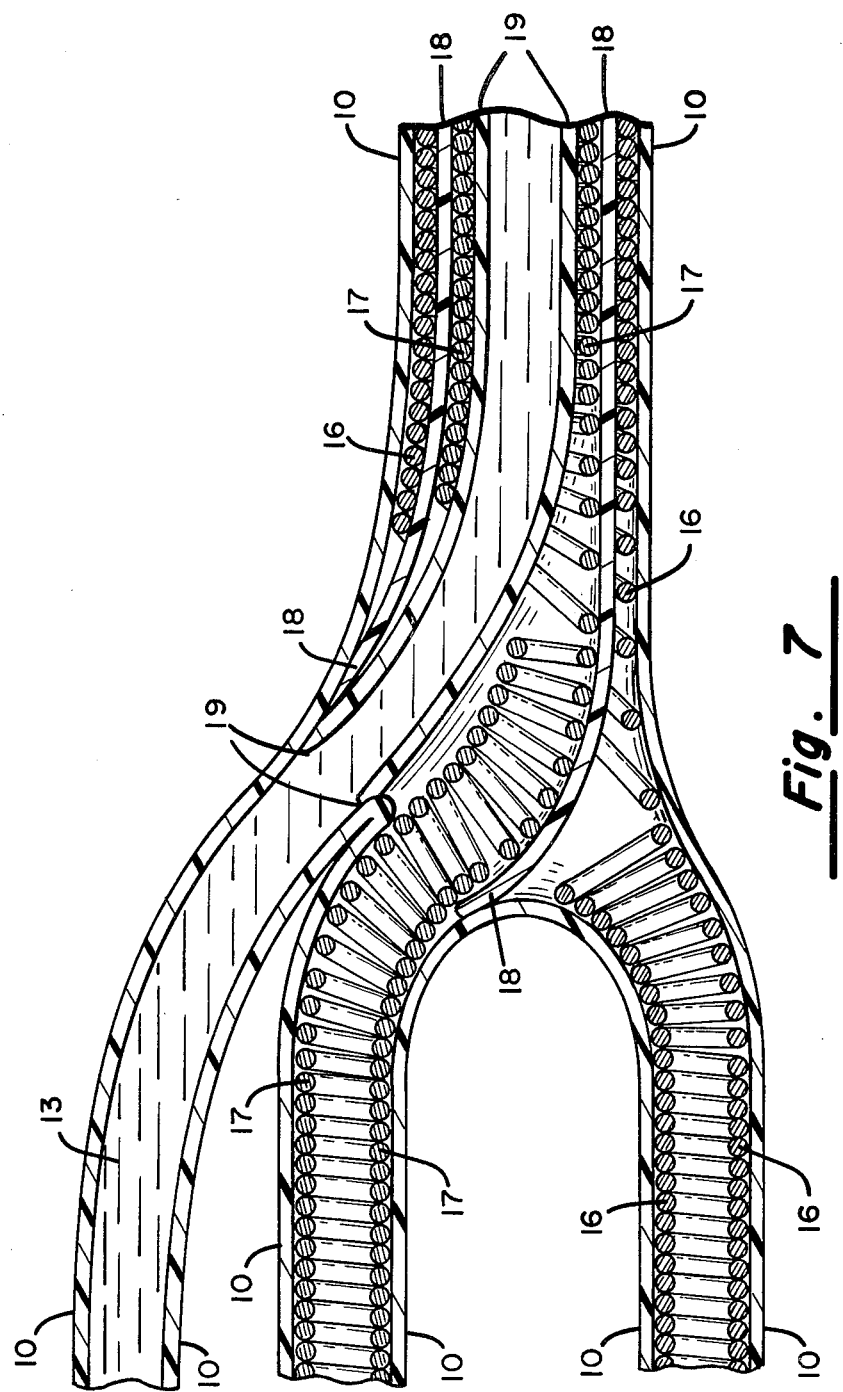
FIG. 7 is a top sectional view of connector 20.

FIG. 7 is a top sectional view showing a portion of connector 20. Outer sheath 10 is shown as covering the entire assembly. Outer conductor 16 goes to connector pin 22b. Inner conductor 17 goes to connector pin 22a. See also FIG. 1. Intermediate sheath 18 terminates as outer conductor 16 and inner conductor 17 separate.

Inner sheath 19 extends through fluid coupling arm 26. As explained above, fluid coupling arm 26 must not have sharp bends causing difficulty for insertion of the stylet. Reference 13 indicates the position of the stylet during implantation and the flow of a chemical agent during dispensing or irrigation.

Figure 8:
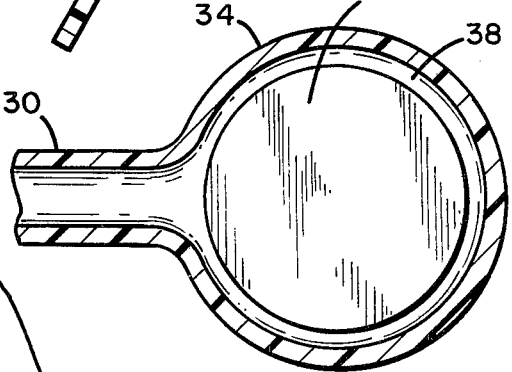
FIG. 8 is a top sectional view of bladder 34.

FIG. 8 is a top sectional view of bladder 34. Notice that tubing 30 may be molded directly to bladder 34, which simply becomes a flat enlargement of tubing 30. Metal plate 36 is located within bladder 34 to prevent a hypodermic syringe from puncturing both walls of bladder 34 enabling the chemical agent to be dispensed external to bladder 34. Metal plate 36 is also opaque to diagnostic radiation permitting bladder 34 to be readily located under fluoroscopy.

Figure 9:
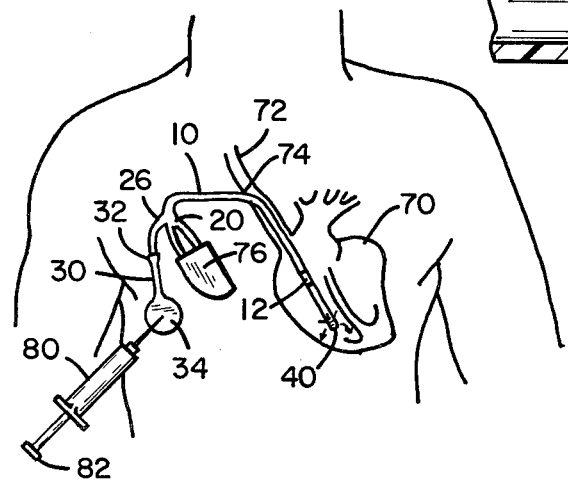
FIG. 9 schematically shows post-implant irrigation of endocardial tissue using the present invention.

FIG. 9 is a schematic view of the preferred embodiment in use. The distal end of the pacing lead is placed into vein 72 at aperture 74. Ring tip electrode 40 is caused to be located at the apex of the right ventricle of the heart 70. The proximal end of the pacing lead is arranged such that pulse generator 76 may be conveniently located and connected via connector 20. Tubing 30 is coupled to fluid coupling arm 26 via fluid connector 32. Bladder 34 is implanted subcutaneously at a convenient location.

At some time subsequent to implant, the attending physician may administer a chemical agent by percutaneously inserting hypodermic syringe 80 into bladder 34. Pressure on plunger 82 causes the chemical agent to be transferred from hypodermic syringe 80 to bladder 34 and thence into heart 70 from the apertures in ring tip electrode 40 as shown.

The preferred mode of a bipolar pacing lead having been disclosed, those skilled in the art will readily be able to design a unipolar pacing lead incorporating the present invention.

What is claimed is:

1. An endocardial pacing lead suitable for chronic implantation comprising:
an insulative outer sheath having a proximal end and a distal end;
a first conductor having a proximal end and a distal end fixedly mounted within said outer sheath;
a fluid resistant inner sheath having a proximal end, a distal end, and an interior lumen, fixedly mounted within said outer sheath;
a first electrode electrically coupled to the distal end of said first conductor and fixedly attached to the distal end of said outer sheath, said first electrode having an exterior surface exposed to the exterior of said outer sheath and at least one aperture open to both the exterior surface of said electrode and to the lumen of said inner sheath;

a first electrical connector electrically coupled to the proximal end of said first conductor and fixedly attached to said outer sheath; and an implantable fluid chamber fixedly attached to the proximal end of said inner sheath and in fluid communication with the lumen of said inner sheath.

2. An endocardial pacing lead according to claim 1 wherein said first conductor is a helically wound coil.

3. An endocardial pacing lead according to claim 2 wherein said inner sheath is located coaxially within said first conductor.

4. An endocardial pacing lead according to claim 3 further comprising:

a second conductor having a proximal end and a distal end;

a second electrode electrically coupled to the distal end of said second conductor and fixedly attached to said outer sheath proximal to said first electrode;

an intermediate sheath coupled to said second conductor and insulating said second conductor from said first conductor; and a second electrical connector electrically coupled to the proximal end of said second conductor and fixedly attached to said outer sheath.

5. An endocardial pacing lead according to claim 4 wherein said first conductor and said second conductor are each a helically wound coil.

6. An endocardial pacing lead according to claim 5 wherein said intermediate sheath is located coaxially within said second conductor, said first conductor is located coaxially within said intermediate sheath, and said inner sheath is located coaxially within said first conductor.

7. An endocardial pacing lead according to claim 1 or claim 2 or claim 3 or claim 4 or claim 5 or claim 6 wherein said fluid chamber is of a material which is sealably punctured percutaneously by a hypodermic syringe whereby fluids may be transferred from said hypodermic syringe to said fluid chamber and thence to said inner sheath and thence from said at least one aperture of said first electrode.

8. An endocardial pacing lead according to claim 7 further comprising:

means fixedly attached at said distal end of said inner sheath for preventing ingress of body fluids from said at least one aperture of said first electrode into said inner sheath.

9. An endocardial pacing lead according to claim 8 wherein said means for preventing ingress of body fluid comprises at least one reed valve.

10. An endocardial pacing lead according to claim 7 wherein said fluid chamber is substantially rigid whereby the interior volume of said chamber remains substantially constant during the introduction of fluid into said chamber.

11. An endocardial pacing lead according to claim 10 further comprising fluid connector means located intermediate said proximal end of said inner sheath and said fluid chamber for disconnecting said fluid chamber from said inner sheath whereby a stylet may be inserted into said inner sheath.

12. An endocardial pacing lead according to claim 11 wherein said fluid chamber is further comprised of a disc of puncture resistant material mounted within said fluid chamber.

13. An endocardial pacing lead suitable to chronic implantation comprising:

an insulative outer sheath having a proximal end and a distal end;

a first conductor having a proximal end and a distal end, mounted within said outer sheath;

a fluid resistant inner sheath having a proximal end, a distal end and an interior lumen, fixedly mounted within said outer sheath;

a first electrode fixedly attached to the distal end of said outer sheath and electrically coupled to said distal end of said first conductor, said electrode having an exterior surface exposed to the exterior of said outer sheath and at least one aperture open to both the interior lumen of said inner sheath and to the exterior surface of said electrode;

a first electrical connector fixedly attached to said outer sheath and electrically coupled to the proximal end of said first conductor; and an implantable substantially rigid fluid chamber fixedly attached to the proximal end of said inner sheath and in fluid communication with the lumen of said inner sheath, said fluid chamber comprised of a material which may be sealably punctured percutaneously by a hypodermic syringe whereby fluids may be transferred from said hypodermic syringe to said fluid chamber and thence to said inner sheath and thence through the at least one aperture of said first electrode.

14. An endocardial pacing lead according to claim 13 further comprising means fixedly attached at the distal end of said inner sheath for preventing ingress of body fluids from the at least one aperture of said first electrode into the lumen of said inner sheath.

15. An endocardial pacing lead according to claim 14 wherein said means for preventing ingress of body fluids comprises at least one reed valve.

16. An endocardial pacing lead according to claim 15 further comprising fluid connector means located intermediate said proximal end of said inner sheath and said fluid chamber for disconnecting said fluid chamber from said inner sheath whereby a stylet may be inserted into said inner sheath.

17. An endocardial pacing lead according to claim 16 wherein said fluid chamber further comprises a disc of puncture resistant material mounted within said fluid chamber.

18. A lead according to claim 13 or claim 14 or claim 15 or claim 16 or claim 17 further comprising:

a second conductor having a proximal end and a distal end, mounted within said inner sheath;

an insulative means mounted between said first conductor and said second conductor whereby said first conductor is electrically insulated from said second conductor;

a second electrode fixedly mounted on said outer sheath, proximal to said first electrode, electrically coupled to the distal end of said second conductor; and a second electrical connector fixedly attached to said outer sheath and electrically coupled to the proximal end of said second conductor.

* * * * *